(12) United States Patent
Zablocki et al.

(10) Patent No.: US 6,403,567 B1
(45) Date of Patent: Jun. 11, 2002

(54) N-PYRAZOLE A2A ADENOSINE RECEPTOR AGONISTS

(75) Inventors: Jeff A. Zablocki, Mountain View; Elfatih O. Elzein, Freemont; Venkata P. Palle, Mountain View, all of CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 09/338,185

(22) Filed: Jun. 22, 1999

(51) Int. Cl.[7] .................. A61K 31/70; C07H 19/167
(52) U.S. Cl. .............. 514/46; 536/27.3; 536/27.6; 536/27.61; 536/27.62; 536/27.63
(58) Field of Search ................. 514/46; 536/27.3, 536/27.6, 27.61, 27.62, 27.63

(56) References Cited

U.S. PATENT DOCUMENTS

| | | | |
|---|---|---|---|
| 4,956,345 A | 9/1990 | Miyasaka et al. ............. 514/46 |
| 4,968,697 A | * 11/1990 | Hutchison ..................... 514/46 |
| 5,189,027 A | 2/1993 | Miyashita et al. ............ 514/46 |
| 5,270,304 A | 12/1993 | Kogi et al. .................... 514/46 |
| 5,459,254 A | 10/1995 | Yamaguchi et al. ..... 536/27.11 |
| 5,593,975 A | 1/1997 | Cristalli ....................... 514/46 |
| 5,705,491 A | 1/1998 | Yamada ....................... 514/46 |
| 5,770,716 A | 6/1998 | Khan et al. ................ 536/23.1 |
| 5,939,543 A | 8/1999 | Morozumi et al. ....... 536/27.63 |

FOREIGN PATENT DOCUMENTS

| | | |
|---|---|---|
| CA | 965411 | 4/1975 |
| EP | 354 638 | 2/1990 |
| JP | Hei 5[1993]-9197 | 1/1993 |

OTHER PUBLICATIONS

Marumoto, et al., "Synthesis and Coronary Vadodilating Activity of 2–Substituted Adenosines", *Chem.. Pharm. Bull.* 23(4): 759–774 (1975).

Marumoto, et al., "Synthesis and Enzymatic Activity of Adenosine 3',5'–Cyclic Phosphate Analogs", *Chem.. Pharm. Bull.* 27(4) 990–1003 (1979).

Persson, et al., "Synthesis and Antiviral Effects of 2–Heteroaryl Substituted Adenosine and 8–Heteroaryl Substituted Guanosine Derivatives", *Bioorganic & Medicinal Chemistry*, 3:1377–1382 (1995).

Mager, et al., "Molecular simulation applied to 2–(N'alkylidenehydrazino)–and 2–(N'–aralkylidenehydrazino) adenosine $A_2$ Agnonists", *Eur J. Med. Chem*, 30:15–25 (1995).

Cristalli et al., "2–Alkynl Derivatives of Adenosine 5'–N'ethyluronamide: Selective $A_2$ Adenosine Receptor Agonists with Potent Inhibitory Activity on Platelet Aggregation", *J. Med. Chem*, 37:1720–1726 (1994). (May 27, 1994).

Matsuda, et al., "Nucleosides and Nucleotides. 103. 2 – Alkynyladenoines: A Novel Class of Selective Adenosine $A_2$ Receptor Agonists with Potent Antihypertensive Effects", *J. Med. Chem.* 35:241–252 (1992). (Jan. 24, 1992).

* cited by examiner

*Primary Examiner*—Paul J. Killos
*Assistant Examiner*—L. Eric Crane
(74) *Attorney, Agent, or Firm*—McDonnell Boehnen Hulbert & Berghoff

(57) ABSTRACT

2-adenosine N-pyrazole compositions having the following formula:

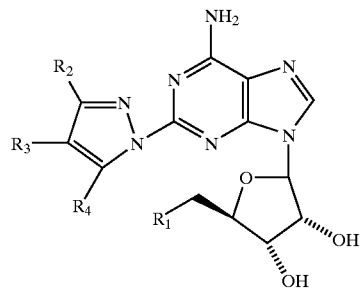

and methods for using the compositions as A2A receptor agonists to stimulate mammalian coronary vasodilatation for therapeutic purposes and for purposes of imaging the heart.

13 Claims, No Drawings

N-PYRAZOLE A2A ADENOSINE RECEPTOR AGONISTS

BACKGROUND OF THE INVENTION

1. Field of Invention

This invention includes N-pyrazole substituted 2-adenosine compositions that are useful as $A_{2A}$ receptor agonists. The compositions of this invention are vasodialating agents that are useful as heart imaging aids that aid in the identification of mammals, and especially humans who are suffering from coronary disorders such poor coronary perfusion which is indicative of coronary artery disease (CAD). The compositions of this invention can also be used as therapeutics for coronary artery disease as well as any other disorders mediated by the $A_{2A}$ receptor.

2. Description of the Art

Pharmacological stress is frequently induced with adenosine or dipyridamole in patients with suspected CAD before imaging with T1 scintigraphy or echocardiography. Both drugs effect dilation of the coronary resistance vessels by activation of cell surface $A_2$ receptors. Although pharmacological stress was originally introduced as a mean of provoking coronary dilation in patients unable to exercise, several studies have shown that the prognostic value of $^{201}$T1 or echocardiographic imaging in patients subjected to pharmacological stress with adenosine or dipyridamole was equivalent to patients subjected to traditional exercise stress tests. However, there is a high incidence of drug-related adverse side effects during pharmacological stress imaging with these drugs such as headache and nausea, that could be improved with new therapeutic agents.

Adenosine $A_{2B}$ and A3 receptors are involved in a mast cell degranulation and, therefore, asthmatics are not give the non-specific adenosine agonists to induce a pharmacological stress test. Additionally, adenosine stimulation of the $A_1$ receptor in the atrium and A-V mode will diminish the S-H interval which can induce AV block (N. C. Gupto et al.; *J. Am Coll. Cardiol*; (1992) 19: 248–257). Also, stimulation of the adenosine $A_1$ receptor by adenosine may be responsible for the nausea since the $A_1$ receptor is found in the intestinal tract (J. Nicholls et al.; *Eur. J. Pharm.* (1997) 338(2) 143–150).

Animal data suggests that specific adenosine $A_{2A}$ subtype receptors on coronary resistance vessels mediate the coronary dilatory responses to adenosine, whereas subtype $A_{2B}$ receptor stimulation relaxes peripheral vessels (note: the latter lowers systemic blood pressure). As a result there is a need for pharmaceutical compositions that are $A_{2A}$ receptor agonists that have no pharmacological effect as a result of stimulating the $A_1$ receptor in vivo. Furthermore, there is a need for $A_{2A}$ receptor agonists that have a short half-life, and that are well tolerated by patients undergoing pharmacological coronary stress evaluations.

SUMMARY OF THE INVENTION

In one aspect, this invention includes 2-adenosine N-pyrazole compositions that are useful $A_{2A}$ receptor agonists.

In another aspect, this invention includes pharmaceutical compositions including 2-adenosine N-pyrazole that are well tolerated with few side effects.

Still another aspect of this invention are N-pyrazole compositions that can be easily used in conjunction with radioactive imaging agents to facilitate coronary imaging.

In one embodiment, this invention includes 2-adenosine N-pyrazole compositions having the following formula:

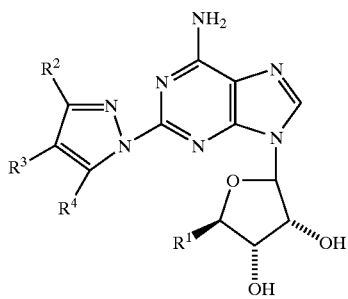

In another embodiment, this invention includes methods for using compositions of this invention to stimulate coronary vasodilatation in mammals, and especially in humans, for stressing the heart induced steal situation for purposes of imaging the heart.

In still another embodiment, this invention is a pharmaceutical composition of matter comprising one or more compositions of this invention and one or more pharmaceutical excipients.

DESCRIPTION OF THE CURRENT EMBODIMENT

This invention includes a new class of 2-adenosine N-pyrazoles having the formula:

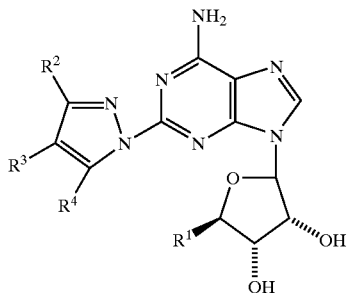

wherein $R^1$=CH$_2$OH, —CONR$_5$R$_6$;

$R^3$ is independently selected from the group consisting of $C_{1-15}$ alkyl, halo, NO$_2$, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$,—CONR$^7$R$^8$, C$_{2-15}$ alkenyl, C$_{2-15}$ alkynyl, heterocyclyl, aryl, and heteroaryl, wherein the alkyl, alkenyl, alkynyl, aryl, heterocyclyl and heteroaryl substituents are optionally substituted with from 1 to 3 substituents independently selected from the group consisting of halo, alkyl, NO$_2$, heterocyclyl, aryl, heteroaryl, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$^2$NR$^{20}$CO$_2$R$^{22}$, SO$_2$NR$^{20}$CON(R$^{20}$)$_2$, N(R$^{20}$)$_2$, NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$_{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$ and wherein the optional substituted heteroaryl, aryl, and heterocyclyl substituents are optionally substituted with halo, NO$_2$, alkyl, CF$_3$, amino, mono- or di-alkylamino, alkyl or aryl or heteroaryl amide, NCOR$^{22}$, NR$^{20}$SO$_2$R$^{22}$, COR$^{20}$, CO$_2$R$^{20}$, CON(R$^{20}$)$_2$, NR$^{20}$CON $(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^5$ and $R^6$ are each individually selected from H, and $C_1$–$C_{15}$ alkyl that is optionally substituted with from 1 to 2 substituents independently selected from the group of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ wherein each optional substituted heteroaryl, aryl, and heterocyclyl substituent is optionally substituted with halo, $NO_2$, alkyl, $CF_3$, amino, monoalkylamino, dialkylamino, alkylamide, arylamide, heteroarylamide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^7$ is selected from the group consisting of hydrogen, $C_{1-15}$ alkyl, $C_{2-15}$ alkenyl, $C_{2-15}$ alkynyl, heterocyclyl, aryl and heteroaryl, wherein the alkyl, alkenyl, alkynyl, aryl, heterocyclyl and heteroaryl substituents are optionally substituted with from 1 to 3 substituents independently selected from the group of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$ and $OCON(R^{20})_2$ and wherein each optional substituted heteroaryl, aryl and heterocyclyl substituent is optionally substituted with halo, $NO_2$, alkyl, $CF_3$, amino, mono- or di-alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^8$ is selected from the group consisting of hydrogen, $C_{1-15}$ alkyl, $C_{2-15}$ alkenyl, $C_{2-15}$ alkynyl, heterocyclyl, aryl, and heteroaryl, wherein the alkyl, alkenyl, alkynyl, aryl, heterocyclyl, and heteroaryl substituents are optionally substituted with from 1 to 3 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R_{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R_{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional substituted heteroaryl, aryl, and heterocyclyl substituent is optionally substituted with halo, $NO_2$, alkyl, $CF_3$, amino, mono- or di- alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^{20}$ is selected from the group consisting of H, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl;

$R^{22}$ is selected from the group consisting of $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and wherein $R^2$ and $R^4$ are selected from the group consisting of H, $C_{1-6}$ alkyl and aryl, wherein the alkyl and aryl substituents are optionally substituted with halo, CN, $CF_3$, $OR^{20}$ and $N(R^{20})_2$ with the proviso that when $R^2$ is not hydrogen then $R^4$ is hydrogen, and when $R^4$ is not hydrogen then $R^2$ is hydrogen.

In preferred compositions of this invention, $R^3$ is selected from the group consisting of $C_{1-15}$ alkyl, halo, $CF_3$, CN, $OR^{20}$, $SR^{20}$, $S(O)R^{22}$, $SO_2R^{22}$, $SO_2N(R^{20})_2$, $COR^{20}$, $CO_2R^{20}$, —$CONR^7R^8$, aryl and heteroaryl wherein the alkyl, aryl and heteroaryl substituents are optionally substituted with from 1 to 3 substituents independently selected from the group consisting of halo, aryl, heteroaryl, $CF_3$, CN, $OR^{20}$, $SR^{20}$, $S(O)R^{22}$, $SO_2R^{22}$, $SO_2N(R^{20})_2$, $COR^{20}$, $CO_2R^{20}$ or $CON(R^{20})_2$, and each optional heteroaryl and aryl substituent is optionally substituted with halo, alkyl, $CF_3$ CN, and $OR^{20}$; $R^5$ and $R^6$ are independently selected from the group of H and $C_1$–$C_{15}$ alkyl including one optional aryl substituent and each optional aryl substituent that is optionally substituted with halo or $CF_3$; $R^7$ is selected from the group consisting of $C_{1-15}$ alkyl, $C_{2-15}$ alkynyl, aryl, and heteroaryl, wherein the alkyl, alkynyl, aryl, and heteroaryl substituents are optionally substituted with from 1 to 3 substituents independently selected from the group consisting of halo, aryl, heteroaryl, $CF_3$, CN, $OR^{20}$, and each optional heteroaryl and aryl substituent is optionally substituted with halo, alkyl, $CF_3$, CN, or $OR^{20}$; $R^8$ is selected from the group consisting of hydrogen and $C_{1-15}$ alkyl; $R^{20}$ is selected from the group consisting of H, $C_{1-4}$ alkyl and aryl, wherein alkyl and aryl substituents are optionally substituted with one alkyl substituent; and $R^{22}$ is selected from the group consisting of $C_{1-4}$ alkyl and aryl which are each optionally substituted with from 1 to 3 alkyl group.

In more preferred compositions, $R^1$ is $CH_2OH$; $R^3$ is selected from the group consisting of $CO_2R^{20}$, —$CONR^7R^8$ and aryl where the aryl substituent is optionally substituted with from 1 to 2 substituents independently selected from the group consisting of halo, $C_{1-6}$ alkyl, $CF_3$ and $OR^{20}$; $R^7$ is selected from the group consisting of hydrogen, $C_{1-8}$ alkyl and aryl, where the alkyl and aryl substituents are optionally substituted with one substituent selected from the group consisting of halo, aryl, $CF_3$, CN, $OR^{20}$ and wherein each optional aryl substituent is optionally substituted with halo, alkyl, $CF_3$ CN, and $OR^{20}$; $R^8$ is selected from the group consisting of hydrogen and $C_{1-8}$ alkyl; and $R^{20}$ is selected from hydrogen and $C_{1-4}$ alkyl.

In a still more preferred embodiment, $R^1$=$CH_2OH$; $R^3$ is selected from the group consisting of $CO_2R^{20}$, —$CONR^7R^8$, and aryl that is optionally substituted with one substituent selected from the group consisting of halo, $C_{1-3}$ alkyl and $OR^{20}$; $R^7$ is selected from of hydrogen, and $C_{1-3}$ alkyl; $R^8$ is hydrogen; and $R^{20}$ is selected from hydrogen and $C_{1-4}$ alkyl. In this preferred embodiment, $R^3$ is most preferably selected from —$CO_2Et$ and —$CONHEt$.

In another still more preferred embodiment, $R^1$=—$CONHEt$, $R^3$ is selected from the group consisting of $CO_2R^{20}$, —$CONR^7R^8$, and aryl in that aryl is optionally substituted with from 1 to 2 substituents independently selected from the group consisting of halo, $C_{1-3}$ alkyl, $CF_3$ or $OR^{20}$; $R^7$ is selected from the group consisting of hydrogen, and $C_{1-8}$ alkyl that is optionally substituted with one substituent selected from the group consisting of halo, $CF_3$, CN or $OR^{20}$; $R^8$ is selected from the group consisting of hydrogen and $C_{1-3}$ alkyl; and $R^{20}$ is selected from the group consisting of hydrogen and $C_{1-4}$ alkyl. In this more preferred embodiment, $R^8$ is preferably hydrogen, $R^7$ is preferably selected from the group consisting of hydrogen, and $C_{1-3}$, and $R^{20}$ is preferably selected from the group consisting of hydrogen and $C_{1-4}$ alkyl.

In a most preferred embodiment, the composition of this invention is selected from ethyl1-{9-[(4S,2R,3R,5R)-3,4-dihydroxy-5-(hydroxymethyl)oxolan-2-yl]-6-aminopurin-2-yl}pyrazole-4-carboxylate, (4S,2R,3R,5R)-2-{6-amino-2-[4-(4-chlorophenyl)pyrazolyl]purin-9-yl}-5-(hydroxymethyl)oxolane-3,4-diol, (4S,2R,3R,5R)-2-{6-amino-2-[4-(4-methoxyphenyl)pyrazolyl]purin-9-yl}-5-(hydroxymethyl)oxolane-3,4-diol, (4S,2R,3R,5R)-2-{6-amino-2-[4-(4-methylphenyl)pyrazolyl]purin-9-yl}-5-(hydroxymethyl) oxolane-3,4-diol, (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide, 1-{9-[(4S,2R,3R,5R)-3,4-dihydroxy-5-(hydroxymethyl)oxolan-2-yl]-6-aminopurin-2-yl}pyrazole-4-carboxylic acid, and mixtures thereof.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'"R"", where R is lower alkyl, or substituted lower alkyl, R', R'", R"" may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R—Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R—HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

The compounds of this invention can be prepared as outlined in Schemes 1–4. Compounds having the general formula IV can be prepared as shown in Scheme 1.

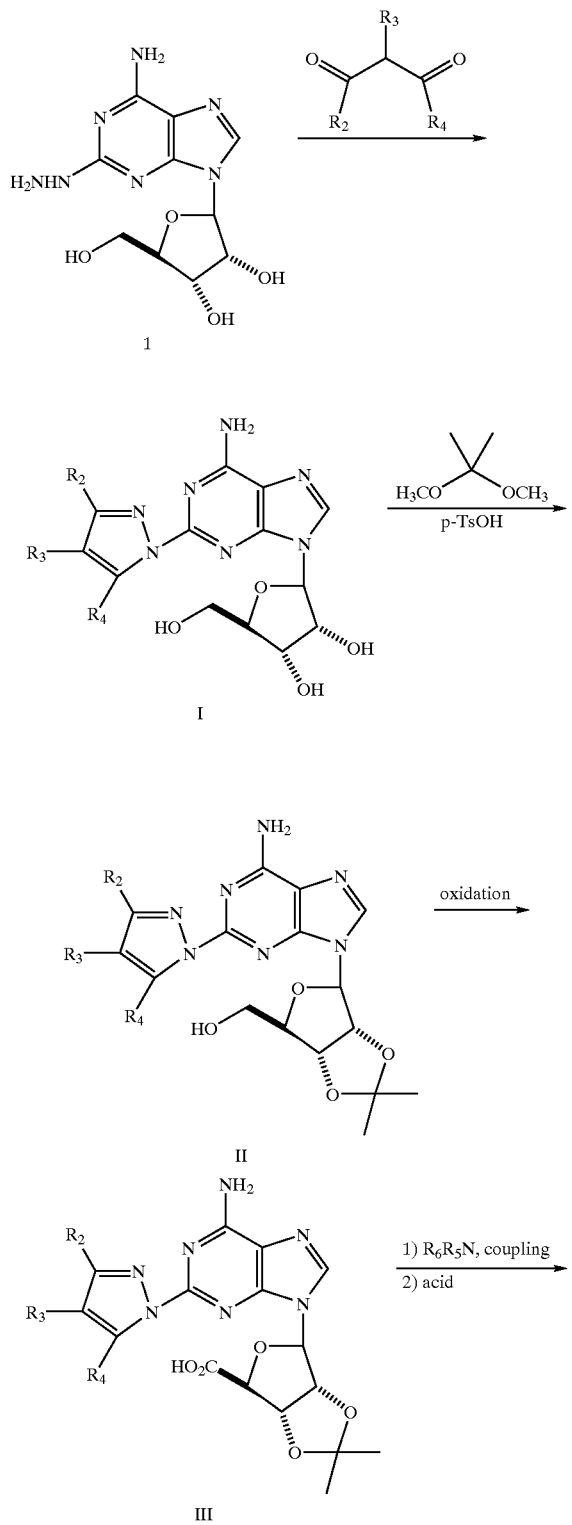

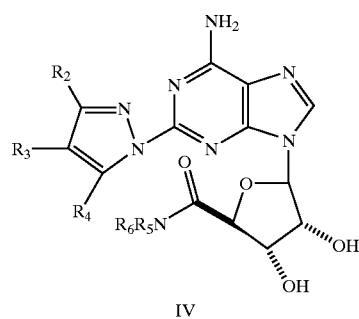

Compound I can be prepared by reacting compound 1 with appropriately substituted 1,3 -dicarbonyl in a mixture of AcOH and MeOH at 80° C. (Holzer et al., J. Heterocycl. Chem. (1993) 30, 865). Compound II, which can be obtained by reacting compound I with 2,2-dimethoxypropane in the presence of an acid, can be oxidized to the carboxylic acid III, based on structurally similar compounds using potassium permanganate or pyridinium chlorochromate (M. Hudlicky, (1990) Oxidations in Organic Chemistry, ACS Monographs, American Chemical Society, Washington D.C.). Reaction of a primary or secondary amine having the formula $HNR^6R^7$, and compound III using DCC (M. Fujino et al., Chem. Pharm. Bull. (1974), 22, 1857), PyBOP (J. Martinez et al., J. Med. Chem. (1988) 28, 1874) or PyBrop (J. Caste et al. Tetrahedron, (1991), 32, 1967) coupling conditions can afford compound IV.

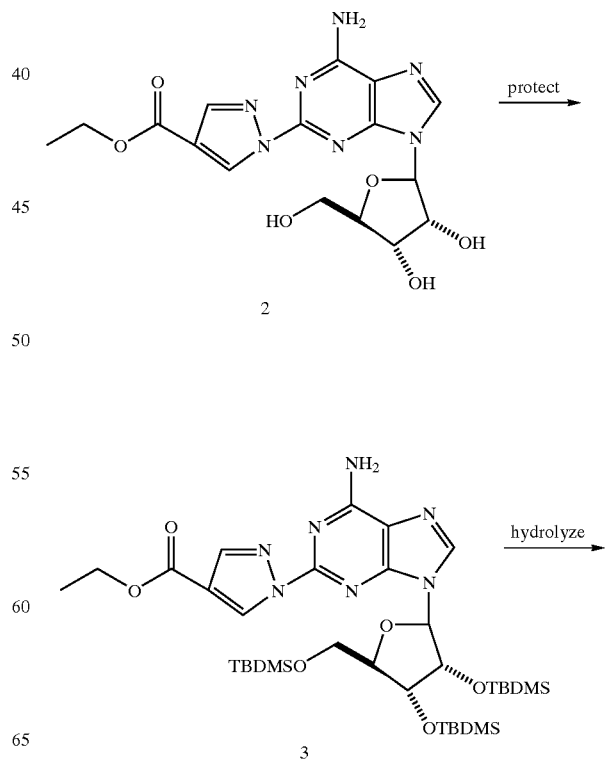

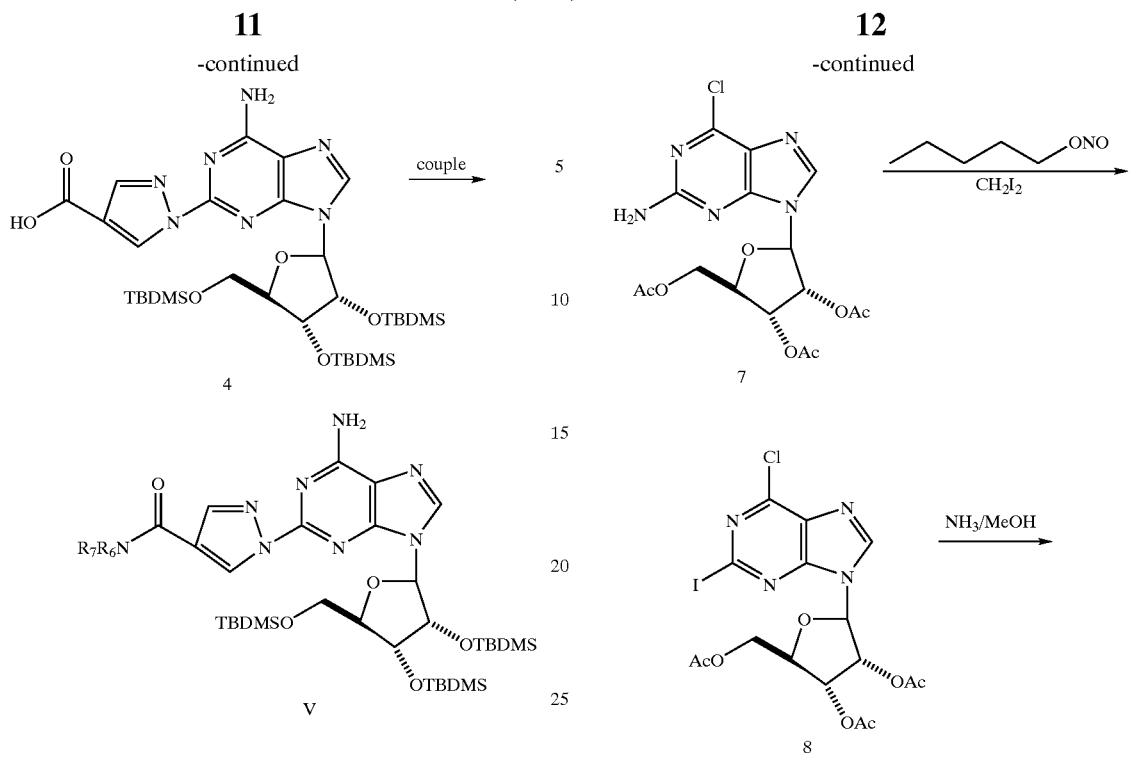

Compound V can be prepared as shown in Scheme 2. The Tri TBDMS derivative 4 can be obtained by treating compound 2 with TBDMSCl and imidazole in DMF followed by hydrolysis of the ethyl ester using NaOH. Reaction of a primary or secondary amine with the formula $HNR^6R^7$, and compound 4 using DCC (M. Fujino et al., Chem. Pharm. Bull. (1974), 22, 1857), PyBOP (J. Martinez et al., J. Med. Chem. (1988) 28, 1874) or PyBrop (J. Caste et al. Tetrahedron, (1991), 32, 1967) coupling conditions can afford compound V.

Scheme 3

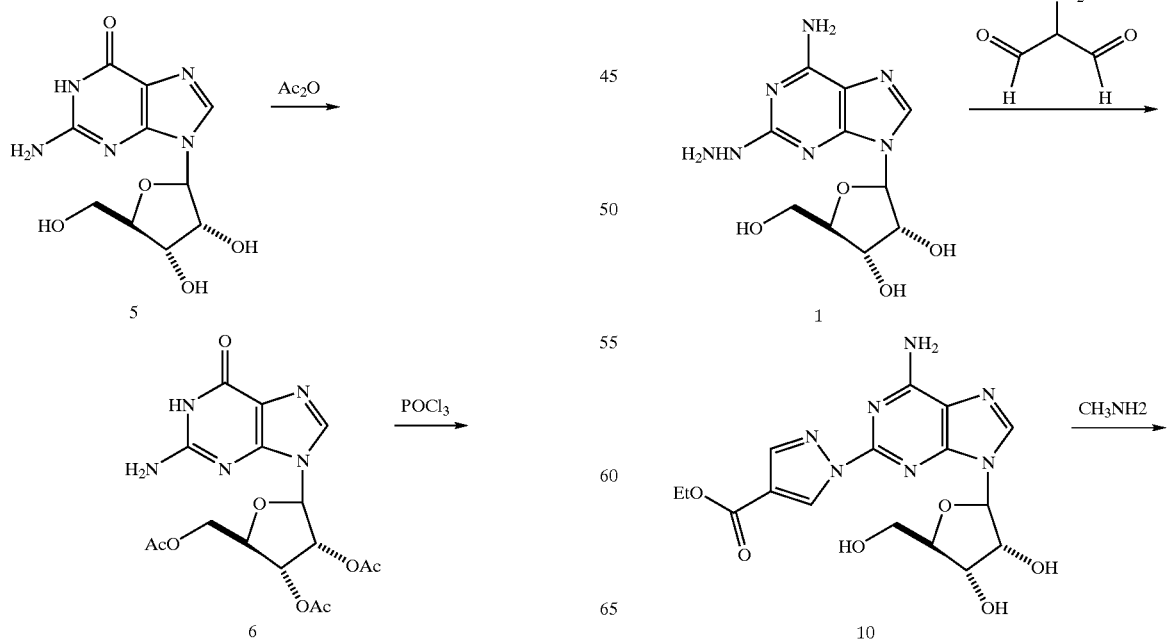

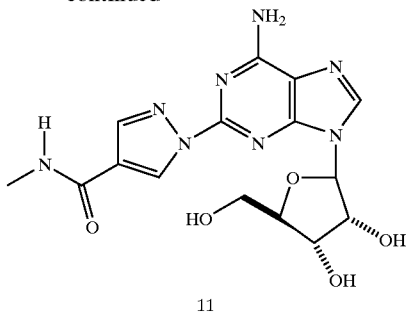

11

A specific synthesis of compound 11 is illustrated in Scheme 3. Commercially available guanosine 5 was converted to the triacetate 6 as previously described (M. J. Robins and B. Uznanski, Can. J. Chem. (1981), 59, 2601–2607). Compound 7, prepared by following the literature procedure of Cerster et al. (J. F. Cerster, A. F. Lewis, and R. K. Robins, Org. Synthesis, 242–243), was converted to compound 9 in two steps as previously described (V. Nair et al., J. Org. Chem., (1988), 53, 3051–3057). Compound 1 was obtained by reacting hydrazine hydrate with compound 9 in ethanol at 80° C. Condensation of compound 1 with ethoxycarbonylmalondialdehyde in a mixture of AcOH and MeOH at 80° C. produced compound 10. Heating compound 10 in excess methylamine afforded compound 11.

Scheme 4

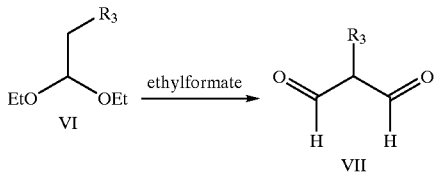

The synthesis of 1,3-dialdehyde VII is described in Scheme 4. Reaction of 3,3-diethoxypropionate or 3,3-diethoxypropionitrile or 1,1-diethoxy-2-nitroethane VI ($R_3$= $CO_2R$, CN or $NO_2$) with ethyl or methyl formate in the presence of NaH can afford the dialdehyde VII (Y. Yamamoto et al., J. Org. Chem. (1989) 54, 4734).

Compounds of this invention are useful in conjunction with radioactive imaging agents to image coronary activity. The compounds of this invention are $A_{2A}$ agonists that are believed to provide specific activation of adenosine $A_{2A}$ receptors in the coronary vessels as opposed to adenosine A1 receptors in the atrium and AV-node and/or $A_{2B}$ receptors in peripheral vessels, thus avoiding undesirable side-effects. Upon administration in a therapeutic amount, the compositions of this invention cause coronary blood vessels to vasodilate to induce coronary steal wherein healthy coronary vessels steal blood from unhealthy vessels resulting in lack of blood flow to heart tissues. Lower doses of the $A_{2A}$ agonists may provide beneficial coronary vasodilatation (less severe) in the treatment of chronic CAD.

As $A_{2A}$ agonists, the compositions of this invention are also useful in adjunctive therapy with angioplasty to induce dilation, inhibit platelet aggregation, and as a general anti-inflammatory agent. $A_{2A}$ agonists, such as the compositions of this invention, can provide the therapeutic benefits described above by preventing neutrophil activation (Purinergic Approaches in Experimental Therapeutics K. A. Jacobson and M. F. Jarvis 1997 Wiley, N.Y.). The compounds of this invention are also effective against a condition called no-reflow in which platelets and neutrophils aggregate and block a vessel. As $A_{2A}$ agonists, the compositions of this invention are effective against no-reflow by preventing neutrophil and platelet activation (e.g., they are believed to prevent release of superoxide from neutrophils). As $A_{2A}$ agonists, the compositions of this invention are also useful as cardioprotective agents through their anti-inflammatory action on neutrophils. Thus, in situations when the heart will go through an ischemic state such as a transplant, they will be useful.

This invention also includes pro-drugs of the above-identified $A_{2A}$ agonists. A pro-drug is a drug which has been chemically modified and may be biological inactive at its site of action, but which will be degraded or modified by one or more enzymatic or in vivo processes to the bioactive form. The pro-drugs of this invention should have a different pharmacokinetic profile to the parent enabling improved absorption across the mucosal epithelium, better salt formulation and/or solubility and improved systemic stability. The above-identified compounds may be preferably modified at one or more of the hydroxyl groups. The modifications may be (1) ester or carbamate derivatives which may be cleaved by esterases or lipases, for example; (2) peptides which may be recognized by specific or non specific proteinase; or (3) derivatives that accumulate at a site of action through membrane selection or a pro-drug form or modified pro-drug form, or any combination of (1) to (3) above.

The compositions may be administered orally, intravenously, through the epidermis or by any other means known in the art for administering a therapeutic agents. The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient. This dose is typically administered in a solution about 5 minutes to about an hour or more prior to coronary imaging. No unacceptable toxicological effects are expected when compounds of the invention are administered in accordance with the present invention.

If the final compound of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution.

Such liquid formulations are suitable for parenteral administration, but may also be used for oral administration. It may be desirable to add excipients such as polyvinylpyrrolidinone, gelatin, hydroxycellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule. It is preferred that the compositions of this invention are administered as a solution either orally or intravenously.

The Examples which follow serve to illustrate this invention. The Examples are intended to in no way limit the scope of this invention, but are provided to show how to make and use the compounds of this invention. In the Examples, all temperatures are in degrees Centigrade.

EXAMPLE 1

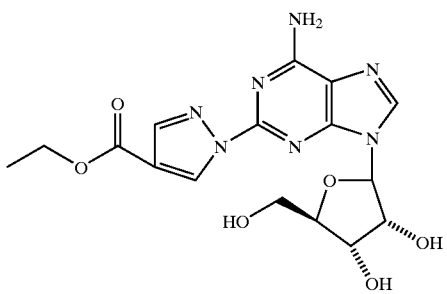

Ethyl 1-{9-[(4S,2R,3R,5R)-3,4-dihydroxy-5-(hydroxymethyl)oxolan-2-yl]-6-aminopurin-2-yl}pyrazole-4-carboxylate which can also be identified as 2-(4-ethoxycarbonylpyrazol-1-yl)adenosine (12)

To a suspension of 2-hydrazinoadenosine (0.025 g, 0.08 mmol) in a 1:1 mixture of MeOH/AcOH was added (ethoxycarbonyl)malondialdehyde ((0.019 g, 0.12 mmol) and the mixture was heated [heated] at 80° C. for 3 h. The precipitate formed was collected by filtration and washed with EtOH and ether to afford 12. $^1$HNMR (DMSO-d6) δ1.25 (t, 3 H), 3.5 (m, 1 H), 3.6 (m, 1 H), 3.8 (d, 1 H), 4.15 (d, 1 H), 4.55 (m, 1H), 5.0 (t, 1 H), 5.2 (d, 1 H), 5.5 (d, 1 H), 5.9 (d, 1H), 7.15–7.3 (m, 5 H), 7.8 (br s, 2 H), 8.1 (s, 1H), 8.4 (s, 1 H), 8.9 (s, 1H).

EXAMPLE 2

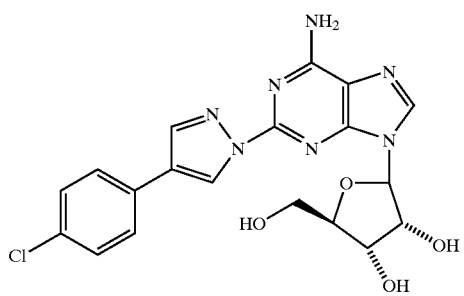

(4S,2R,3R,5R)-2-{6-amino-2-[4-(4-chlorophenyl)pyrazolyl]purin-9-yl}-5-(hydroxymethyl)oxolane-3,4-diol which can also be identified as 2-[4-(4-chlorophenyl)pyrazol-1-yl)]adenosine (13)

To a suspension of 2-hydrazinoadenosine (0.025 g, 0.08 mmol) in a 1:1 mixture of MeOH/AcOH was added 2-(4-chloro)malondialdehyde (0.022 g, 0.12 mmol) and the mixture was heated at 80° C. for 3 h. The precipitate formed was collected by filtration and washed with EtOH and Ether to afford 13. $^1$HNMR (DMSO-d6) δ3.5 (m, 1 H), 3.6 (m, 1 H), 3.8 (d, 1 H), 4.15 (d, 1 H), 4.2 (q, 2 H), 4.55 (m, 1H), 5.9 (d, 1H), 7.45 (d, 2 H), 7.75 (d, 2 H), 8.25 (s, 1H), 8.35 (s, 1 H), 8.9 (s, 1H).

EXAMPLE 3

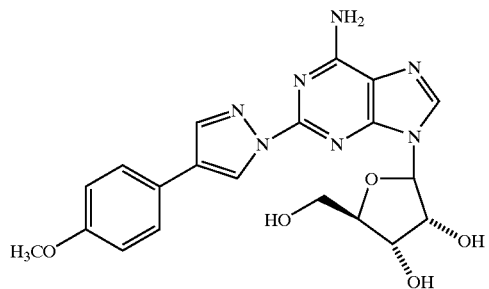

(4S,2R,3R,5R)-2-{6-amino-2-[4-(4-methoxyphenyl)pyrazolyl]purin-9-yl}-5-(hydroxymethyl)oxolane-3,4-diol which can also be identified as 2-[4-(4-methoxyphenyl)pyrazol-1-yl)]adenosine (14)

To a suspension of 2-hydrazinoadenosine (0.025 g, 0.08 mmol) in a 1:1 mixture of MeOH/AcOH was added 2-(4-methoxy)malondialdehyde (0.022 g, 0.12 mmol) and the mixture was heated at 80° C. for 3 h. The precipitate formed was collected by filtration and washed with EtOH and Ether to afford 14. $^1$HNMR (DMSO-d6) δ3.55 (m, 1 H), 3.65 (m, 1 H), 3.75 (s, 3 H), 3.9 (d, 1 H), 4.15 (d, 1 H), 4.6 (m, 1 H), 5.9 (d, 1 H), 6.75 (d, 2 H), 7.6 (d, 2 H), 8.15 (s, 1H), 8.35 (s, 1 H), 8.8 (s, 1 H).

EXAMPLE 4

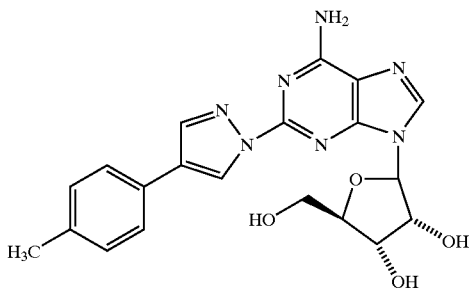

(4S,2R,3R,5R)-2-{6-amino-2-[4-(4-methylphenyl) pyrazolyl]purin-9-yl}-5-(hydroxymethyl)oxolane-3, 4-diol which can also be identified as 2-[4-(4-methylphenyl)pyrazol-1-yl)]adenosine (15)

To a suspension of 2-hydrazinoadenosine (0.025 g, 0.08 mmol) in a 1:1 mixture of MeOH/AcOH was added 2-(4-methyl)malondialdehyde (0.019 g, 0.12 mmol) and the mixture was heated at 80° C. for 3 h. The precipitate formed was collected by filtration and washed with EtOH and Ether to afford 15. $^1$HNMR (DMSO-d6) δ3.55 (m, 1 H\), 3.65 (m, 1 H), 3.75 (s, 3 H), 3.9 (d, 1 H), 4.15 (d, 1 H), 4.6 (m, 1 H), 5.9 (d, 1 H), 6.75 (d, 2 H), 7.6 (d, 2 H), 8.15 (s, 1 H), 8.35 (s, 1 H), 8.8 (s, 1 H).

EXAMPLE 5

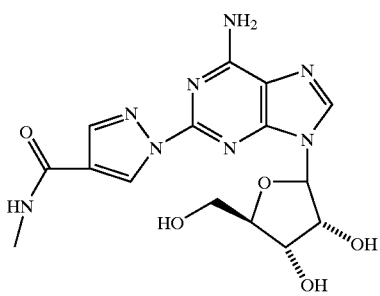

(1-{9-[(4S,2R,3R,5R)-3,4-dihydroxy-5-(hydroxymethyl)oxolan-2-yl]-6-aminopurin-2 - yl}pyrazol-4N-methylcarboxamide which can also be identified as 2-(4-methylaminocarbonylpyrazol-1-yl)adenosine (16)

The mixture heated at 65° C. in for 24 h. After concentration in vacuo, the residue was purified using prep. TLC (10% MeOH:DCM). $^1$HNMR (CD$_3$OD) δ2.90 (s, 3 H), 3.78 (m, 1 H), 3.91 (m, 1 H), 4.13 (d, 1 H), 4.34 (d, 1 H), 4.64 (m, 1 H), 6.06 (d, 1 H), 8.11 (s, 1 H), 8.38 (s, 1 H), 9.05 (s, 1 H).

EXAMPLE 6

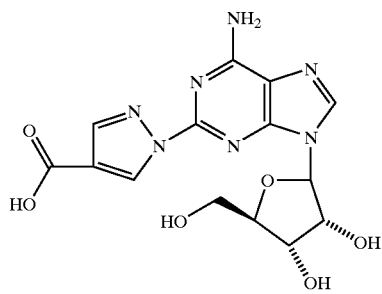

1-{9-[(4S,2R,3R,5R)-3,4-dihydroxy-5-(hydroxymethyl)oxolan-2-yl]-6-aminopurin-2-yl}pyrazole-4-carboxylic acid which can also be identified as 2-(4-carboxypyrazol-1-yl)adenosine (17)

Compound 12 (0.05 mg, 0.12 mmol) was dissolved one equivalent of 1N NaOH. The solution was allowed to stir at Rt for 2 h, then acidified to pH 4. The resulting precipitate was filtered and washed with water and ether. $^1$HNMR (CD$_3$OD) Δ3.75 (m, 1 H), 3.90 (m, 1 H), 4.13 (d, 1 H), 4.43 (d, 1 H), 4.64 (m, 1H), 6.05 (d, 1H), 8.10 (s, 1H), 8.35 (s, 1 H), 9.05 (s, 1 H).

EXAMPLE 7

Compositions of this invention were assayed to determine their affinity for the A2A receptor in a pig striatum membrane prep. Briefly, 0.2 mg of pig striatal membranes were treated with adenosine deaminase (2 U/ mL) and 50 mM Tris buffer (pH=7.4) followed by mixing. To the pig membranes was added 2 μL of serially diluted DMSO stock solution of the compounds of this invention at concentrations ranging from 10 nM to 100 microM or the control received 2 microL of DMSO alone, then the trotted antagonist ZM 241385 in Tris buffer (50 mM, pH of 7.4) was added to achieve a final concentration of 2 nM . After incubation at 23° C. for 2 h, then the solutions were filtered using a membrane harvester using multiple washing of the membranes (3x). The filter disks were counted in scintillation cocktail to determine the amount of displacement of tritiated ZM displaced by the compositions of this invention. Greater than a 5 point curve was used to generate Ki's. and the number of experiments is indicated in the column marked in Table 1 below.

TABLE 1

| Compound Number | $A_{2a}$ Ki, nM | n |
|---|---|---|
| 12 | +++ | 2 |
| 13 | ++ | 3 |
| 14 | ++ | 1 |
| 15 | ++ | 3 |
| 16 | ++ | 2 |
| 17 | − | 1 |

+++ = 10–1,000 nM
++ = 1,000–10,000 nM
+ = greater than 10,000 nM
− = greater than 100,000 nM

What we claim is:

1. A compound having the formula:

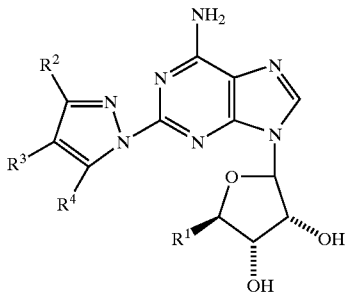

wherein
- $R^1$ is —$CH_2OH$;
- $R^2$ and $R^4$ are each hydrogen;
- $R^3$ is selected from the group consisting of $CO_2R^{20}$, —$CONR^7R^8$ and aryl wherein the aryl substituent is optionally substituted with from 1 to 2 substituents independently selected from the group consisting of halo, $C_{1-6}$ alkyl, $CF_3$ and $OR^{20}$;
- $R^7$ is selected from the group consisting of hydrogen, $C_{1-8}$ alkyl and aryl, wherein the alkyl and aryl substituents are optionally substituted with one substituent selected from the group consisting of halo, aryl, $CF_3$, CN, and $OR^{20}$ and wherein each optional aryl substituent is optionally substituted with at least one substituent selected from the group consisting of halo, alkyl, $CF_3$ CN, and $OR^{20}$;
- $R^8$ is selected from the group consisting of hydrogen and $C_{1-8}$ alkyl; and
- $R^{20}$ is selected from the group consisting of hydrogen and $C_{1-8}$ alkyl.

2. The compound of claim 1 wherein $R^3$ is selected from the group consisting of $CO_2R^{20}$, —$CONR^7R^8$, and aryl that is optionally substituted with from 1 to 2 substituents independently selected from the group consisting of halo, $C_{1-3}$ alkyl, $CF_3$ and $OR^{20}$;
- $R^7$ is selected from the group consisting of hydrogen, and $C_{1-8}$ alkyl that is optionally substituted with one substituent selected from the group consisting of halo, $CF_3$, CN and $OR^{20}$;
- $R^8$ is selected from the group consisting of hydrogen and $C_{1-3}$ alkyl; and
- $R^{20}$ is selected from the group consisting of hydrogen and $C_{1-4}$ alkyl.

3. The compound of claim 1 wherein $R^3$ is selected from the group consisting of $CO_2R^{20}$, —$CONR^7R^8$, and aryl that is optionally substituted with one substituent selected from the group consisting of halo, $C_{1-3}$ alkyl, and $OR^{20}$;
- $R^7$ is selected from the group consisting of hydrogen, and $C_{1-3}$ alkyl that is optionally substituted with one substituent selected from the group consisting of halo, $CF_3$, CN and $OR^{20}$;
- $R^8$ is hydrogen; and
- $R^{20}$ is selected from the group consisting of hydrogen and $C_{1-4}$ alkyl.

4. The compound of claim 1 wherein $R^3$ is selected from the group consisting of $CO_2R^{20}$, —$CONR^7R^8$, and aryl that is optionally substituted with one substituent selected from the group consisting of halo, $C_{1-3}$ alkyl and $OR^{20}$;
- $R^7$ is selected from the group consisting of hydrogen, and $C_{1-3}$ alkyl;
- $R^8$ is hydrogen; and
- $R^{20}$ is selected from the group consisting of hydrogen and $C_{1-4}$ alkyl.

5. The compound of claim 4 wherein $R^7$ is a methyl.

6. The compound of claim 4 wherein $R^3$ is —$CO_2Et$.

7. The compound of claim 1 selected from the group consisting of 2-(4-methylaminocarbonylpyrazol-1-yl) adenosine; 2-(4-ethoxycarbonylpyrazol-1-yl)adenosine; 2-[4-(4-chlorophenyl)pyrazol-1-yl)]adenosine; 2-[4-(4-methoxyphenyl)pyrazol-1-yl)]adenosine; 2-[4-(4-methylphenyl)pyrazol-1-yl)]adenosine; and 2-(4-carboxypyrazol-1-yl)adenosine.

8. A compound having the following formula:

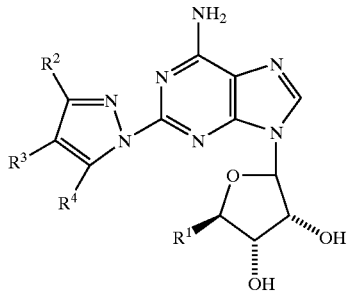

wherein
- $R^1$ is —$CH_{20}OH$;
- $R^2$ and $R^4$ are each hydrogen;
- $R^3$ is —$CONR^7R^8$;
- $R^7$ is methyl; and
- $R^8$ is hydrogen.

9. A pharmaceutical composition comprising a compound of claim 1 and one or more pharmaceutically acceptable excipients.

10. The pharmaceutical composition of claim 9 wherein the pharmaceutical composition is in the form of a solution.

11. A method for stimulating coronary vasodilation in a mammal by administering to the mammal a therapeutically effective amount of a compound of claim 1 that is sufficient to stress the heart and induce a coronary steal situation for the purposes of imaging the heart.

12. The method of claim 11 wherein the therapeutically effective amount ranges from about 0.01 to about 100 mg/kg weight of the mammal.

13. The method of claim 11 wherein the mammal is a human.

* * * * *

UNITED STATES PATENT AND TRADEMARK OFFICE
CERTIFICATE OF CORRECTION

PATENT NO. : 6,403,567 B1  Page 1 of 1
APPLICATION NO. : 09/338185
DATED : June 11, 2002
INVENTOR(S) : Zablocki et al.

It is certified that error appears in the above-identified patent and that said Letters Patent is hereby corrected as shown below:

Column 20,
Line 37, delete "-CH$_{20}$OH" and replace with -- -CH$_2$OH --.

Signed and Sealed this

Twentieth Day of June, 2006

JON W. DUDAS
*Director of the United States Patent and Trademark Office*

UNITED STATES PATENT AND TRADEMARK OFFICE
CERTIFICATE OF CORRECTION

PATENT NO. : 6,403,567 B1  Page 1 of 1
APPLICATION NO. : 09/338185
DATED : June 11, 2002
INVENTOR(S) : Zablocki et al.

It is certified that error appears in the above-identified patent and that said Letters Patent is hereby corrected as shown below:

At column 17, line 56, delete "4N" and replace with -- 4-yl)-N --

Signed and Sealed this

Ninth Day of September, 2008

JON W. DUDAS
*Director of the United States Patent and Trademark Office*

UNITED STATES PATENT AND TRADEMARK OFFICE
CERTIFICATE OF CORRECTION

Page 1 of 1

| | |
|---|---|
| PATENT NO. | : 6,403,567 B1 |
| APPLICATION NO. | : 09/338185 |
| DATED | : June 11, 2002 |
| INVENTOR(S) | : Zablocki et al. |

It is certified that error appears in the above-identified patent and that said Letters Patent is hereby corrected as shown below:

At column 17, line 62, before the word "The" add the sentence -- Compound 12 (0.05 mg, 0.12 mmol) was added to 4 mL methylamine (40% sol. in water). --

Signed and Sealed this

Thirteenth Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,403,567 B1 | Page 1 of 1 |
| APPLICATION NO. | : 09/338185 | |
| DATED | : June 11, 2002 | |
| INVENTOR(S) | : Jeff A. Zablocki et al. | |

It is certified that error appears in the above-identified patent and that said Letters Patent is hereby corrected as shown below:

Front Page
Field (57), in the Abstract, the word "vasodilatation" should be replaced with --vasodilation--.

Column 20
Line 52, the word "purposes" should be replaced with --purpose--.

Signed and Sealed this

Twenty-fifth Day of October, 2011

David J. Kappos
*Director of the United States Patent and Trademark Office*

UNITED STATES PATENT AND TRADEMARK OFFICE
CERTIFICATE OF CORRECTION

PATENT NO. : 6,403,567 B1
APPLICATION NO. : 09/338185
DATED : June 11, 2002
INVENTOR(S) : Zablocki, Elzein and Palle Page 1 of 4

It is certified that error appears in the above-identified patent and that said Letters Patent is hereby corrected as shown below:

TITLE PAGE, ITEM (57) ABSTRACT

" 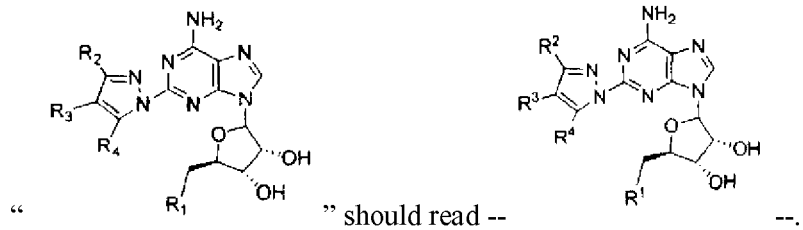 " should read -- --.

IN THE SPECIFICATION
Column 1
Line 11, "such poor" should read --such as poor--;
Line 22, "mean" should read --means--;
Line 30, "drugs such" should read --drugs, such--;
Line 32, "A3" should read --$A_3$--;
Line 32, "in a mast" should read --in mast--;
Line 33, "give" should read --given--;
Line 36, "A-V mode" should read --AV node--;
Line 40, "for the nausea" should read --for nausea--;
Line 60, "N-pyrazole" should read --N-pyrazoles--.

Column 2
Line 17, "vasodilatation" should read --vasodilation--;
Line 18, "induced" should read --and inducing a--;
Line 42, "$R^1$ =CH$_2$OH, -CONR$_5$R$_6$" should read --$R^1$ = CH$_2$OH or -CONR$^5$R$^6$--;
Line 60, "CON(R$_{20}$)$_2$" should read --CON(R$^{20}$)$_2$--;
Line 63, delete "substituted" after optional.

Column 3
Line 5, "group of" should read --group consisting of--;

Signed and Sealed this
Eighth Day of May, 2012

David J. Kappos
*Director of the United States Patent and Trademark Office*

CERTIFICATE OF CORRECTION (continued)

Line 13, delete "substituted" after optional;
Line 17, "CON(R$^{20)}_2$" should read --CON(R$^{20}$)$_2$--;
Line 25, "the group of" should read --the group consisting of--;
Line 28, "NR$^{20}$CO$_2$R$_{22}$," should read --NR$^{20}$CO$_2$R$^{22}$,--;
Lines 32 and 52, delete "substituted" after optional;
Line 47, "N(R$_{20}$)$_2$," should read --N(R$^{20}$)$_2$,--;
Line 49, "CON(R$_{20}$)$_2$," should read --CON(R$^{20}$)$_2$,--.

Column 4
Lines 22 and 49, "CF$_3$ CN" should read --CF$_3$, CN--;
Line 23, "group of" should read --group consisting of--;
Line 23, "C$_1$-C$_{15}$" should read --C$_{1-15}$--;
Line 24, "substituent and" should read --substituent, and--;
Line 24, delete "that";
Lines 30 and 47, "CN, OR$^{20}$" should read --CN, and OR$^{20}$--;
Line 38, "group" should read --groups--;
Line 56, "from of hydrogen," should read --from hydrogen--;
Line 62, "in that aryl is" should read --wherein the aryl substituent is--;
Line 66, "hydrogen, and" should read --hydrogen and--.

Column 5
Line 6, "C$_{1-3}$" should read --C$_{1-3}$ alkyl--;
Line 9, "ethyl1-{" should read --ethyl 1-{--.

Column 6
Line 28, "branched alkenyl" should read --branched alkynyl--.

Column 7
Line 2, "by" should read --be--;
Line 3, "hetaryl, substituted hetaryl" should read --hetaryl, or substituted hetaryl--.

Column 8
Line 2, "Heterocycyl" should read --Heterocyclyl--;
Line 12, "mono or poly substituted" should read --mono- or poly-substituted--.

Column 9

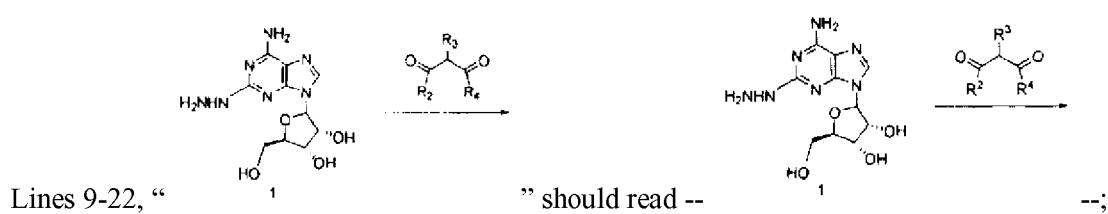

Lines 9-22, " " should read -- --;

CERTIFICATE OF CORRECTION (continued)
U.S. Pat. No. 6,403,567 B1

Lines 24-36, " 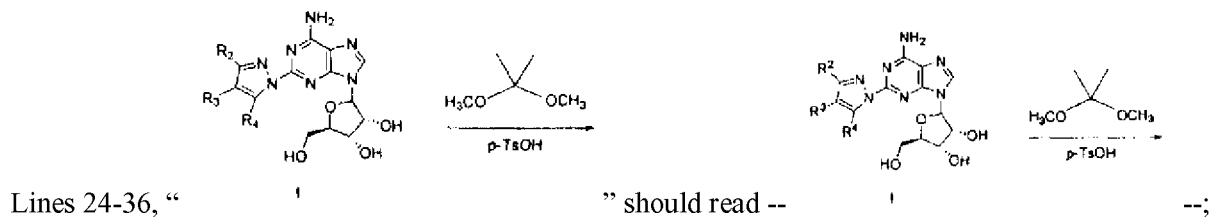 " should read -- --;

Lines 39-52, " 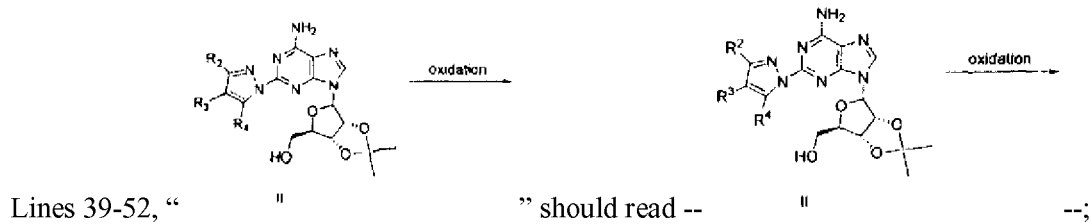 " should read -- --;

Lines 53-65, " 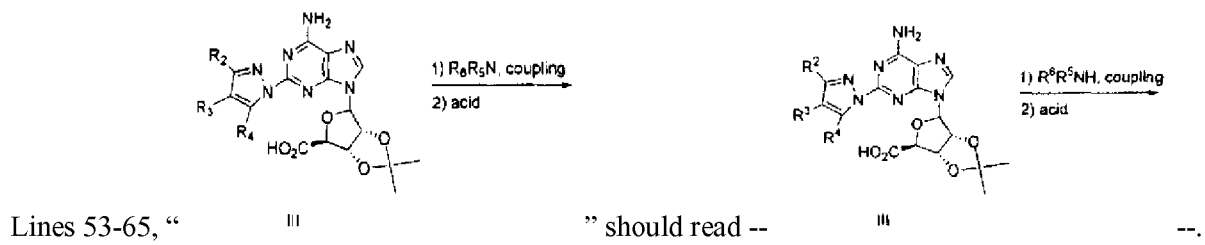 " should read -- --.

Column 10

Lines 2-15, " 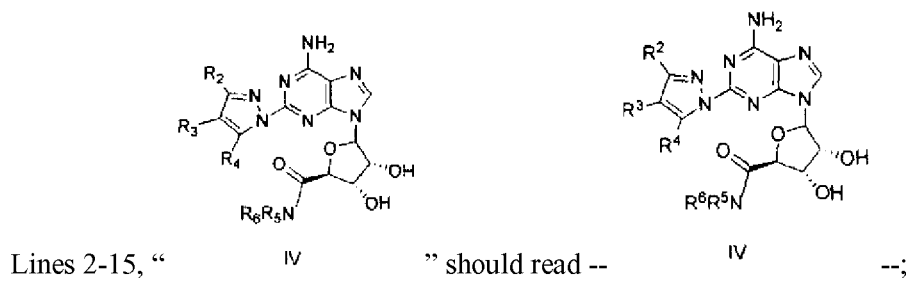 " should read -- --;

Line 30, "$HNR^6R^7$" should read --$HNR^6R^5$--.

Column 11

Lines 15-25, " 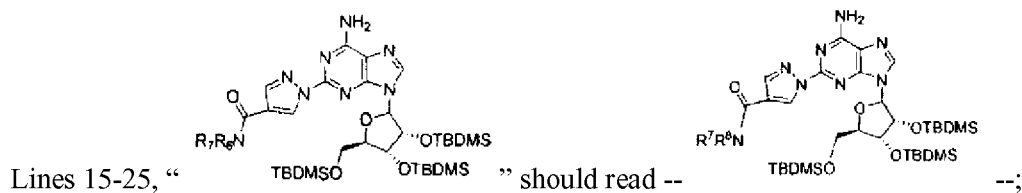 " should read -- --;

Line 34, "$HNR^6R^7$" should read --$HNR^7R^8$--.

Column 12
Line 57, "CH3NH2" should read --CH$_3$NH$_2$--.

Column 13
Line 27, "80 ° C." should read --80° C--;

Lines 31-39, "  " should read -- --;
Line 50, "A1" should read --A$_1$--;
Line 51, "AV-node" should read --AV node--;
Line 52, "side-effects" should read --side effects--;
Line 58, "vasodilatation" should read --vasodilation--.

Column 14
Line 14, "biological" should read --biologically--;
Line 25, "proteinase" should read --proteinases--;
Line 31, "agents" should read --agent--.

Column 15
Line 60, "((0.019 g, 0.12 mmol)" should read --(0.019 g, 0.12 mmol)--;
Line 61, "heated [heated]" should read --heated--;
Line 61, "80° C. for" should read --80° C for--.

Column 16
Lines 27 and 62, "80° C. for" should read --80° C for--.

Column 17
Line 28, "80° C. for" should read --80° C for--;
Line 62, "heated at 65° C. in for" should read --was heated at 65° C for--.

Column 18
Line 27, "Δ3.75" should read --δ 3.75--;
Line 35, "A2A" should read --A$_{2A}$--;
Line 45, "nM ." should read --nM.--;
Line 45, "23° C. for" should read --23° C for--;
Line 51, "Ki's." should read --Ki's--.

UNITED STATES PATENT AND TRADEMARK OFFICE
CERTIFICATE OF CORRECTION

| | |
|---|---|
| PATENT NO. | : 6,403,567 B1 |
| APPLICATION NO. | : 09/338185 |
| DATED | : June 11, 2002 |
| INVENTOR(S) | : Zablocki, Elzein and Palle |

It is certified that error appears in the above-identified patent and that said Letters Patent is hereby corrected as shown below:

TITLE PAGE, ITEM (57) ABSTRACT

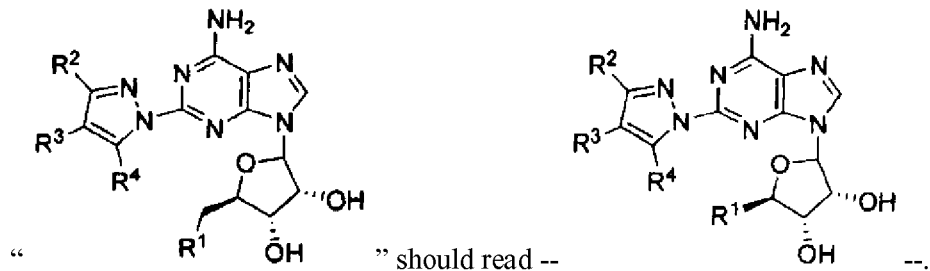

IN THE SPECIFICATION
Column 1
Line 11, "such poor" should read --such as poor--;
Line 22, "mean" should read --means--;
Line 30, "drugs such" should read --drugs, such--;
Line 32, "A3" should read --$A_3$--;
Line 32, "in a mast" should read --in mast--;
Line 33, "give" should read --given--;
Line 36, "A-V mode" should read --AV node--;
Line 40, "for the nausea" should read --for nausea--;
Line 60, "N-pyrazole" should read --N-pyrazoles--.

Column 2
Line 17, "vasodilatation" should read --vasodilation--;
Line 18, "induced" should read --and inducing a--;
Line 42, "$R^1 =CH_2OH, -CONR_5R_6$" should read --$R^1 = CH_2OH$ or $-CONR^5R^6$--;
Line 60, "$CON(R_{20})_2$" should read --$CON(R^{20})_2$--;
Line 63, delete "substituted" after optional.

This certificate supersedes the Certificate of Correction issued May 8, 2012.

Signed and Sealed this
Third Day of July, 2012

David J. Kappos
*Director of the United States Patent and Trademark Office*

Column 3
Line 5, "group of" should read --group consisting of--;
Line 13, delete "substituted" after optional;
Line 17, "CON($R^{20)}_2$" should read --CON($R^{20}$)$_2$--;
Line 25, "the group of" should read --the group consisting of--;
Line 28, "NR$^{20}$CO$_2$R$_{22}$," should read --NR$^{20}$CO$_2$R$^{22}$,--;
Lines 32 and 52, delete "substituted" after optional;
Line 47, "N(R$_{20}$)$_2$," should read --N(R$^{20}$)$_2$,--;
Line 49, "CON(R$_{20}$)$_2$," should read --CON(R$^{20}$)$_2$,--.

Column 4
Lines 22 and 49, "CF$_3$ CN" should read --CF$_3$, CN--;
Line 23, "group of" should read --group consisting of--;
Line 23, "C$_1$-C$_{15}$" should read --C$_{1-15}$--;
Line 24, "substituent and" should read --substituent, and--;
Line 24, delete "that";
Lines 30 and 47, "CN, OR$^{20}$" should read --CN, and OR$^{20}$--;
Line 38, "group" should read --groups--;
Line 56, "from of hydrogen," should read --from hydrogen--;
Line 62, "in that aryl is" should read --wherein the aryl substituent is--;
Line 66, "hydrogen, and" should read --hydrogen and--.

Column 5
Line 6, "C$_{1-3}$" should read --C$_{1-3}$alkyl--;
Line 9, "ethyl1-{" should read --ethyl 1-{--.

Column 6
Line 28, "branched alkenyl" should read --branched alkynyl--.

Column 7
Line 2, "by" should read --be--;
Line 3, "hetaryl, substituted hetaryl" should read --hetaryl, or substituted hetaryl--.

Column 8
Line 2, "Heterocycyl" should read --Heterocyclyl--;
Line 12, "mono or poly substituted" should read --mono- or poly-substituted--.

Column 9
Lines 9-22, " 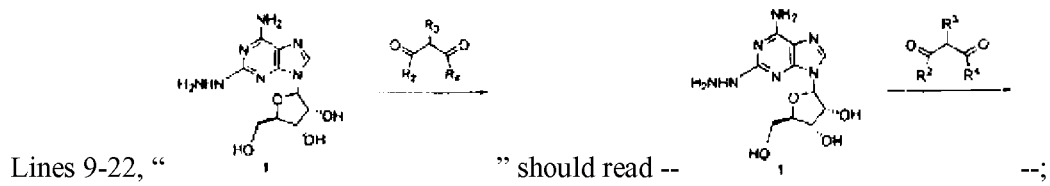 " should read -- --;

CERTIFICATE OF CORRECTION (continued)
U.S. Pat. No. 6,403,567 B1

Lines 24-36, " " should read -- --;

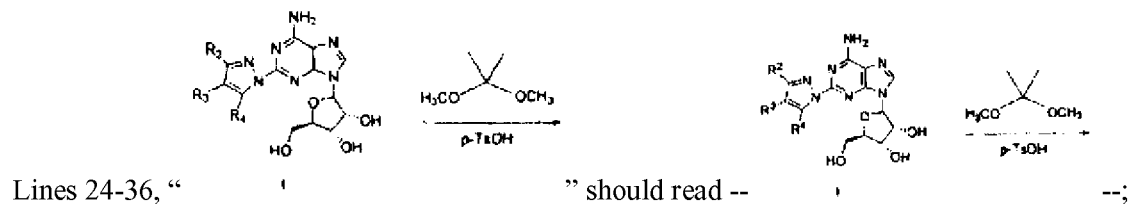

Lines 39-52, " " should read -- --;

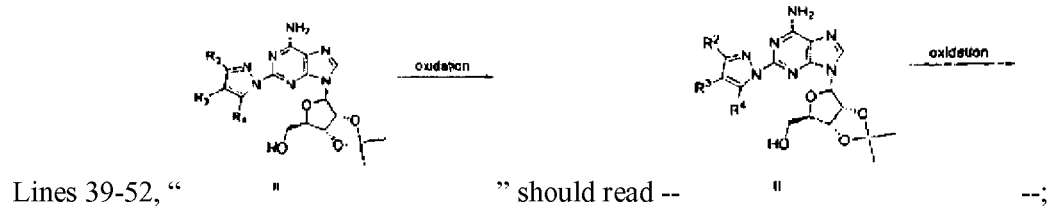

Lines 53-65, " " should read -- --.

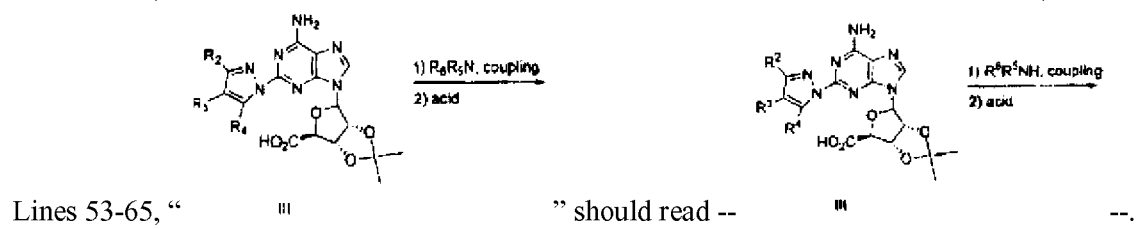

Column 10

Lines 2-15, " " should read -- --;

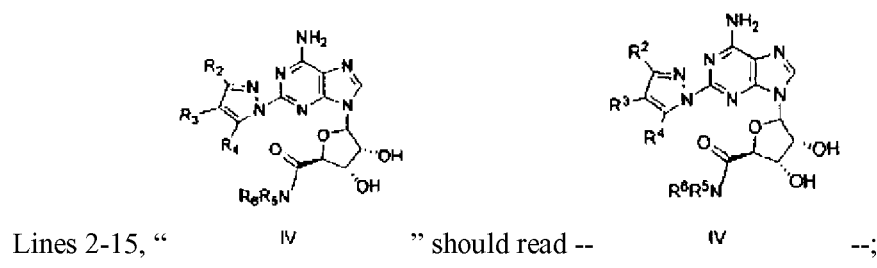

Line 30, "HNR⁶R⁷" should read --HNR⁶R⁵--.

Column 11

Lines 15-25, " " should read -- --;

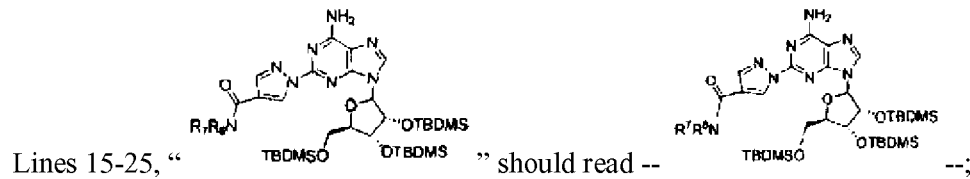

Line 34, "HNR⁶R⁷" should read --HNR⁷R⁸--.

Column 12
Line 57, "CH₃NH2" should read --CH₃NH₂--.

Column 13
Line 27, "80 ° C." should read --80° C--;

Lines 31-39, "  " should read --  --;

Line 50, "A1" should read --$A_1$--;
Line 51, "AV-node" should read --AV node--;
Line 52, "side-effects" should read --side effects--;
Line 58, "vasodilatation" should read --vasodilation--.

Column 14
Line 14, "biological" should read --biologically--;
Line 25, "proteinase" should read --proteinases--;
Line 31, "agents" should read --agent--.

Column 15
Line 60, "((0.019 g, 0.12 mmol)" should read --(0.019 g, 0.12 mmol)--;
Line 61, "heated [heated]" should read --heated--;
Line 61, "80° C. for" should read --80° C for--.

Column 16
Lines 27 and 62, "80° C. for" should read --80° C for--.

Column 17
Line 28, "80° C. for" should read --80° C for--;
Line 62, "heated at 65° C. in for" should read --was heated at 65° C for--.

Column 18
Line 27, "Δ3.75" should read --δ 3.75--;
Line 35, "A2A" should read --$A_{2A}$--;
Line 45, "nM ." should read --nM.--;
Line 45, "23° C. for" should read --23° C for--;
Line 51, "Ki's." should read --Ki's--.

UNITED STATES PATENT AND TRADEMARK OFFICE
Certificate

Patent No. 6,403,567 B1                                                 Patented: June 11, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jeff A. Zablocki, Mountain View, CA (US); Elfatih O. Elzein, Freemont, CA (US); Venkata P. Palle, Mountain View, CA (US); and Luiz Belardinelli, Palo Alto, CA (US).

Signed and Sealed this Twentieth Day of May 2014.

SHAOJIA ANNA JIANG
*Supervisory Patent Examiner*
Art Unit 1623
Technology Center 1600

UNITED STATES PATENT AND TRADEMARK OFFICE
Certificate

Patent No. 6,403,567 B1

Patented: June 11, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jeff A. Zablocki, Mountain View, CA (US); Elfatih O. Elzein, Fremont, CA (US); Venkata P. Palle, Mountain View, CA (US); and Luiz Belardinelli, Palo Alto, CA (US).

Signed and Sealed this Twelfth Day of August 2014.

SHAOJIA ANNA JIANG
*Supervisory Patent Examiner*
Art Unit 1623
Technology Center 1600